United States Patent
Kang et al.

(10) Patent No.: US 9,053,214 B2
(45) Date of Patent: Jun. 9, 2015

(54) APPARATUS FOR COLLECTING LIFELOG DATA AND METHOD THEREOF

(71) Applicant: ELECTRONICS AND TELECOMMUNICATIONS RESEARCH INSTITUTE, Daejeon (KR)

(72) Inventors: Kyu Chang Kang, Daejeon (KR); Seong Uk Heo, Ulsan (KR); Yong Jin Kwon, Seoul (KR); Chang Seok Bae, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 123 days.

(21) Appl. No.: 13/735,486

(22) Filed: Jan. 7, 2013

(65) Prior Publication Data

US 2014/0122541 A1    May 1, 2014

(30) Foreign Application Priority Data

Oct. 29, 2012   (KR) .................. 10-2012-0120421

(51) Int. Cl.
*G06F 7/00* (2006.01)
*G06F 17/30* (2006.01)
*G06F 19/00* (2011.01)
*G06Q 50/24* (2012.01)

(52) U.S. Cl.
CPC .............. *G06F 19/322* (2013.01); *G06Q 50/24* (2013.01)

(58) Field of Classification Search
None
See application file for complete search history.

(56) References Cited

U.S. PATENT DOCUMENTS

2005/0197865 A1*  9/2005  Jordan ............................. 705/3
2010/0333020 A1*  12/2010  Jeong et al. .................. 715/810

FOREIGN PATENT DOCUMENTS

KR    10-2007-0062215    6/2007

* cited by examiner

*Primary Examiner* — Rehana Perveen
*Assistant Examiner* — Raheem Hoffler
(74) *Attorney, Agent, or Firm* — Staas & Halsey LLP (57) ABSTRACT

Disclosed are an apparatus for collecting lifelog data and a method thereof according to the present invention.
The present invention relates to an apparatus for collecting lifelog data and a method thereof, which collect information for analyzing a behavior pattern from devices used by a user in everyday life, convert the collected information according to a preset schema, and provide the converted information.

14 Claims, 5 Drawing Sheets

APPARATUS FOR COLLECTING LIFELOG DATA AND METHOD THEREOF

CROSS-REFERENCE TO RELATED APPLICATIONS

This application claims priority to and the benefit of Korean Patent Application No. 10-2012-0120421 filed in the Korean Intellectual Property Office on Oct. 29, 2012, the entire contents of which are incorporated herein by reference.

TECHNICAL FIELD

The present invention relates to a method of collecting lifelog data, and more particularly, to an apparatus for collecting lifelog data and a method thereof, which collect information for analyzing a behavior pattern from devices used by a user in everyday life, convert the collected information according to a preset schema, and provide the converted information.

BACKGROUND ART

According to a current rapid progress of industrialization, a fatality rate caused by an adult disease sharply increases. It has been revealed that one of the main reasons is due to the lack of exercise, which has resulted in people becoming more interested in exercise. Particularly, people complaining of a body part even though there is no onset of a specific disease have increased in older generations, and diseases including obesity, high blood pressure, and heart disease due to unhealthy everyday lifestyle such as overeating and a lack of exercise, causing injuries including backaches, muscle pain and like due to lack of muscular power have increased. Those are all generated by an unhealthy lifestyle and a chronic lack of exercise, which have recently risen as social issues.

In order to solve the above problems, it is required to determine and improve an unhealthy lifestyle by participating in regular and continuous exercise daily. However, a user who has not been diagnosed with a specific disease symptom does not visit a hospital to receive a physical evaluation nor is prescribed with exercise regimen, which depends on a complicated machine, such that the user has a tendency to neglect the prevention of a chronic disease.

In order to assist a current user's life and an exercise habit, methods including a portable exercise prescribing machine, tailored exercise equipment controlling system and the like based on biometric information or exercise information have been disclosed, but a method of collecting, transmitting, storing, managing, standardizing data from a viewpoint of lifelog of the user and utilizing the data in a $3^{rd}$ party application program has not been disclosed.

SUMMARY OF THE INVENTION

The present invention has been made in an effort to solve the problems occurring in the prior art and an aspect of the present invention is to provide an apparatus for collecting lifelog data and a method thereof, which collect information for analyzing a behavior pattern from devices used by a user in everyday life, convert the collected information according to a preset schema, and provide the converted information.

However, the aspect of the present invention is not limited thereto, and other aspects which have been not mentioned will be apparently understood by those skilled in the art through the following description.

An exemplary embodiment of the present invention provides an apparatus for collecting lifelog data including: an input unit configured to receive information according to a menu or key control from a user; a controller configured to collect measured lifelog data of a first schema from one or more sensing apparatuses through an application activated according to the received information and convert the collected lifelog data of the first schema to lifelog data of a preset second schema; a display unit configured to display an analysis result of a behavior of the user through the application based on the converted lifelog data of the second schema; a storage unit configured to store the lifelog data of the first schema or the lifelog data of the second schema; and a communication unit configured to transmit the lifelog data of the first schema or the lifelog data of the second schema to a lifelog server configured to manage the lifelog data for each user, wherein the application processes data based on the lifelog data of the second schema.

When the lifelog data is collected, the controller may identify whether to have first schema information of the collected lifelog data, and when the controller has the first schema information as a result of the identification, the controller may convert the lifelog data of the first schema to the lifelog data of the second schema by using the first schema information.

When the lifelog data is collected, the controller may identify whether to have first schema information of the collected lifelog data, and when the controller does not have the first schema information as a result of the identification, the controller may download the first schema information from a schema server and convert the lifelog data of the first schema to the lifelog data of the second schema by using the downloaded first schema information.

The display unit may display a sentence of informing the user that the first schema information is automatically downloaded from the schema server and an OK button for confirming the download at one side of the sentence.

When the lifelog data is collected, the controller may identify whether to have first schema information of the collected lifelog data, and when the controller does not have the first schema information as a result of the identification, the controller may ask the user about whether to download the first schema information from the schema server and download the first schema information according to an input selection of the user in response to an inquiry.

The display unit may display a sentence of asking the user about whether to download the first schema information from the schema server and display an acceptance button of accepting the download and a cancellation button of cancelling the download at one side of the sentence.

The controller may collect the measured lifelog data according to schema information preset to each of the one or more sensing apparatuses.

Another exemplary embodiment of the present invention provides a method of collecting lifelog data including: collecting measured lifelog data of a first schema from one or more sensing apparatuses through an application and converting the collected lifelog data of the first schema to lifelog data of a preset second schema; displaying an analysis result of a behavior of a user through the application based on the converted lifelog data of the second schema; storing the lifelog data of the first schema or the lifelog data of the second schema; and transmitting the lifelog data of the first schema or the lifelog data of the second schema to a lifelog server configured to manage the lifelog data for each user, wherein the application processes data based on the lifelog data of the second schema.

In the converting of the collected lifelog data, when the lifelog data is collected, it may be identified whether to have first schema information of the collected lifelog data, and when it is identified to have the first schema information as a result of the identification, the lifelog data of the first schema may be converted to the lifelog data of the second schema by using the first schema information.

In the converting of the collected lifelog data, when the lifelog data is collected, it may be identified whether to have first schema information of the collected lifelog data, and when it is identified not to have the first schema information as a result of the identification, the first schema information may be downloaded from a schema server and the lifelog data of the first schema may be converted to the lifelog data of the second schema by using the downloaded first schema information.

In the converting of the collected lifelog data, a sentence of informing the user that first schema information is automatically downloaded from the schema server may be displayed and an OK button for confirming the download may be displayed at one side of the sentence.

In the converting of the collected lifelog data, when the lifelog data is collected, it may be identified whether to have first schema information of the collected lifelog data, and when it is identified not to have the first schema information as a result of the identification, the user may be asked whether to download the first schema information from the schema server and the first schema information may be downloaded according to an input selection of the user in response to an inquiry.

In the converting of the collected lifelog data, a sentence of asking the user about whether to download the first schema information from the schema server may be displayed and an acceptance button of accepting the download and a cancellation button of cancelling the download may be displayed in one side of the sentence.

In the converting of the collected lifelog data, the measured lifelog data may be collected according to schema information preset to each of the one or more sensing apparatuses.

Accordingly, the present invention has an effect of increasing a quality of a physical examination by collecting information for analyzing a behavior pattern from devices used by a user in everyday life, converting the collected information according to a preset schema, and providing the converted information.

The present invention has an effect of increasing a quality of a medical treatment by collecting information for analyzing a behavior pattern from devices used by a user in everyday life, converting the collected information according to a preset schema, and providing the converted information.

The present invention has an effect of being used in various services by collecting information for analyzing a behavior pattern from devices used by a user in everyday life, converting the collected information according to a preset schema, and providing the converted information.

The foregoing summary is illustrative only and is not intended to be in any way limiting. In addition to the illustrative aspects, embodiments, and features described above, further aspects, embodiments, and features will become apparent by reference to the drawings and the following detailed description.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings.

In the following description, an apparatus for collecting lifelog data and a method thereof according to exemplary embodiments of the present invention will be discussed with reference to accompanying FIGS. 1 to 6. A part required to understand an operation and an effect according to the present invention will be mainly described.

In descriptions of components of the present invention, different reference numerals may be designated to components having the same name, and the same reference numeral may be designated to components in different drawings. However, the cases do not mean that the corresponding component has different functions according to exemplary embodiments or has the same function in different exemplary embodiments, and the function of each component should be determined based on the description of each component in a corresponding exemplary embodiment.

Particularly, the present invention provides a new method of collecting lifelog data for analyzing a behavior pattern from devices used by a user in everyday life, converting the collected lifelog data according to a preset schema, and providing the converted lifelog data.

Figure 1:
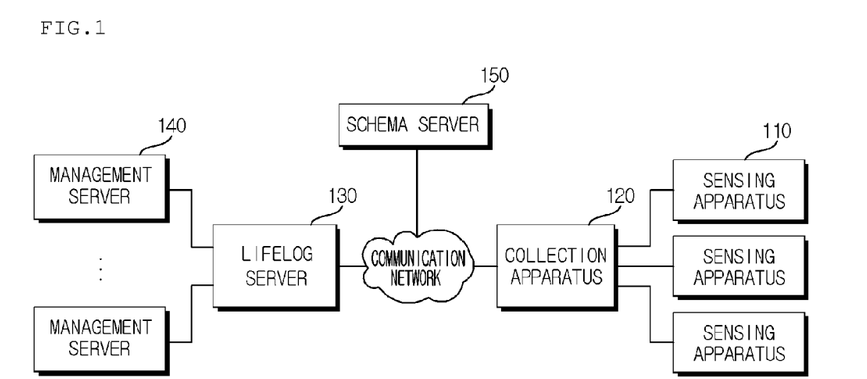
FIG. 1 schematically illustrates a configuration of a total system according to an exemplary embodiment of the present invention.

FIG. 1 schematically illustrates a configuration of a total system according to an exemplary embodiment of the present invention.

As illustrated in FIG. 1, the total system according to the present invention may include a sensing apparatus 110, a collection apparatus 120, a lifelog server 130, a management server 140, a schema server 150, and the like.

The sensing apparatus 110 may obtain lifelog data for analyzing a behavior pattern, for example, biometric information, behavior information, and the like. The sensing apparatus 110 may be installed within the collection apparatus 120 or may be implemented to interwork with the collection apparatus 120 through wired or wireless communication.

For example, the sensing apparatus 110 may include an acceleration sensor, an illumination sensor, a global positioning system (GPS) receiver and the like installed within the collection apparatus 120.

The collection apparatus 120 may activate an application and interwork with at least one sensing apparatus 110 through the activated application to collect measured various lifelog data. The collection apparatus 120 refers to an apparatus used by a user in everyday life and may be, for example, a concept including all of a mobile phone, a smart phone, a tablet PC, a notebook computer and the like.

The collection apparatus 120 may convert the collected lifelog data according to a preset schema. Here, the schema refers to a logical structure of a database expressing information on a structure and a content of the data, and logical and physical properties of the data. The schema may be differently set according to a manufacturer manufacturing the sensing apparatus 110.

At this time, the collection apparatus 120 may convert lifelog data of a first schema differently set for each sensing apparatus 110 to lifelog data of a preset second schema. To this end, the collection apparatus 120 should know the first schema and the second schema in advance, so that the collection apparatus 120 receives the first schema and the second schema from the schema server 150 and stores them.

For example, the collection apparatus 120 converts lifelog data to seven decimal places according to a set first schema to lifelog data to two decimal places according to a preset second schema.

When the collection apparatus 120 does not have information on the first schema differently set for each sensing apparatus 110, the collection apparatus 120 may access the schema server 150 to receive the corresponding schema.

The collection apparatus 120 may store the lifelog data converted according to the preset schema therein or provide the converted lifelog data to the lifelog server 130 through wired or wireless communication.

The lifelog server 130 may receive the lifelog data from the collection apparatus 120 and store the received lifelog data separately for each user.

The lifelog server 130 may provide lifelog data on a corresponding user according to a request of the management server managed by an organization or an institution requiring the lifelog data.

At this time, the lifelog server 130 may convert the pre-stored lifelog data of the first schema to the lifelog data of the second schema requested by the management server. To this end, the lifelog server 130 should know the first schema and the second schema in advance, so that the lifelog server 130 receives the first schema and the second schema from the schema server 150 and stores them.

The management server 140 may receive the lifelog data on the user and provide various types of services to the user based on the received lifelog data.

For example, the management server managed by a hospital may configure a medical examination table based on the lifelog data on the user desired to be treated by the hospital and provide the configured medical examination table to the user.

For another example, the management server managed by a health care company may provide proper exercise prescription based on the lifelog data on the user desired to be managed by the health care company.

The schema server 150 may store schema information on data measured by sensing apparatuses developed and distributed by the manufacturer. The schema information is provided to users after being set to each sensing apparatus and registered in the schema server 150.

Figure 2:
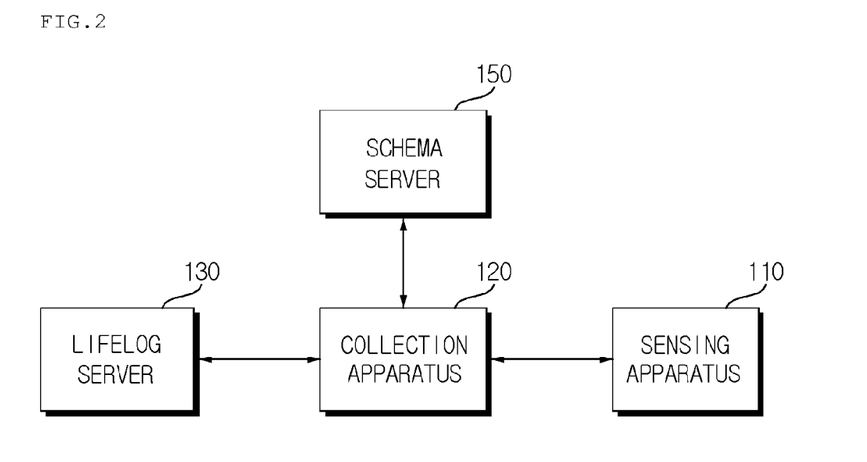
FIG. 2 is a diagram for describing an operation principle of collecting lifelog data.

FIG. 2 is a diagram for describing an operation principle of collecting lifelog data.

As illustrated in FIG. 2, at least one sensing apparatus 110 may interwork with the collection apparatus 120 and obtain the lifelog data for analyzing a behavior pattern of the user.

The collection apparatus 120 may interwork with at least one sensing apparatus 110 through an application to collect the measured various lifelog data from the sensing apparatus 110.

The collection apparatus 120 may identify whether to have schema information on the collected lifelog data. When the collection apparatus has the schema information, the collection apparatus converts the lifelog data of the first schema to the lifelog data of the preset second schema.

On the other hand, when the collection apparatus 120 does not have the schema information, the collection apparatus 120 accesses the schema server 150 to download first schema information from the accessed schema server 150 and converts the lifelog data of the downloaded first schema to the lifelog data of the preset second schema.

The collection apparatus 120 may store the converted lifelog data or provide the converted lifelog data to the lifelog server. At this time, the collection apparatus stores the converted lifelog data in the lifelog server or provides the corresponding lifelog data according to a request of the lifelog server.

Figure 3:
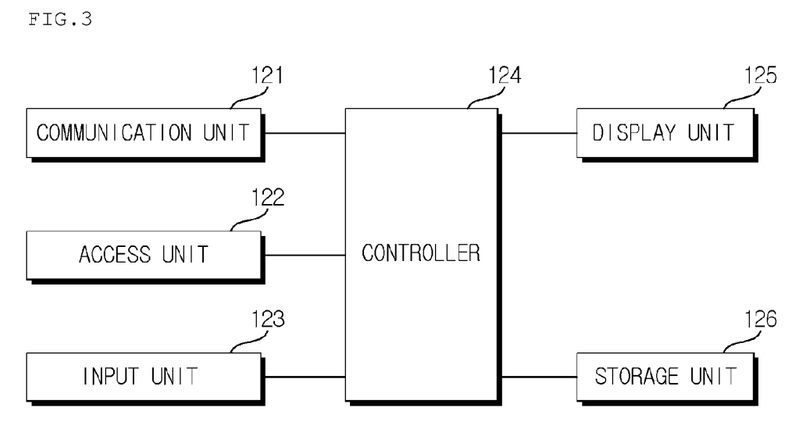
FIG. 3 illustrates a detailed configuration of a collection apparatus 120 according to an exemplary embodiment of the present invention.

FIG. 3 illustrates a detailed configuration of the collection apparatus 120 according to an exemplary embodiment of the present invention.

As illustrated in FIG. 3, the collection apparatus 120 according to the present invention may include a communication unit 121, an access unit 122, an input unit 123, a controller 124, a display unit 125, a storage unit 126, and the like.

The communication unit 121 may interwork with the schema server and the lifelog server to transmit and receive data. At this time, the communication unit 121 may be implemented as one physically combined apparatus to interwork with both the schema server and the lifelog server or implemented as two physically separated apparatuses to interwork with the schema server and the lifelog server, respectively.

The access unit 122 may be connected to at least one sensing apparatus through a wired line or wirelessly.

The input unit 123 may receive information according to a menu or key control from the user.

The controller 124 may activate an application according to the received information and collect measured various lifelog data from at least one sensing apparatus through the activated application.

The controller 124 may identify whether to have schema information on the collected lifelog data. When the collection apparatus 120 has the schema information, the controller 124 converts the lifelog data of the first schema to the lifelog data of the preset second schema.

On the other hand, when the collection apparatus 120 does not have the schema information, the controller 124 accesses the schema server to download first schema information from the accessed schema server and converts the lifelog data of the downloaded first schema to the lifelog data of the preset second schema.

Figure 4A:
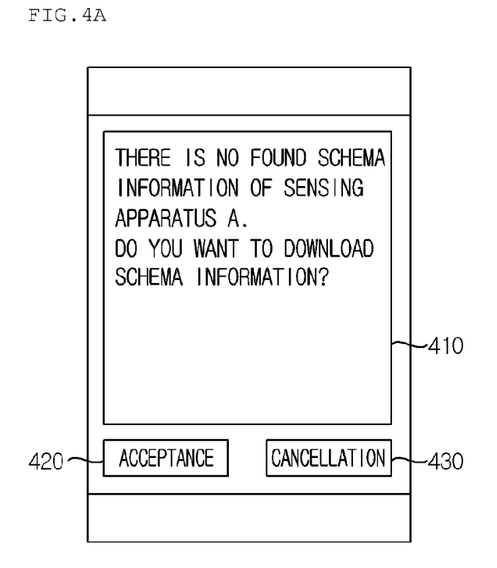
FIGS. 4A and 4B illustrate screens of a display unit within a collection apparatus according to an exemplary embodiment of the present invention.
Figure 4B:
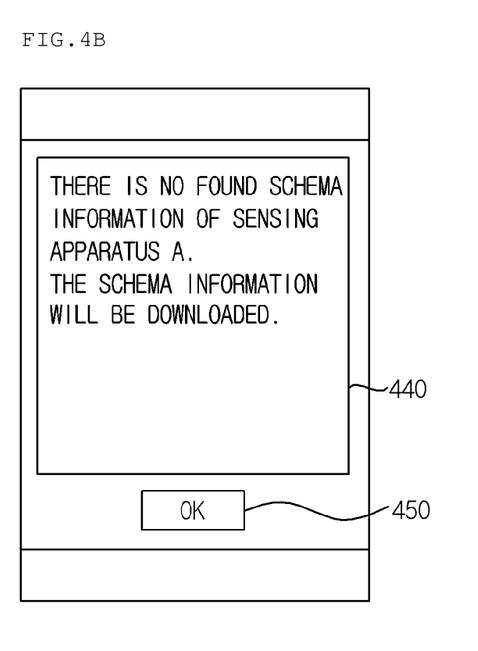

FIGS. 4A and 4B illustrate screens of the display unit within the collection apparatus according to an exemplary embodiment of the present invention.

As illustrated in FIG. 4A, when the collection apparatus does not have the schema information preset to the corresponding sensing apparatus, the collection apparatus may display sentences 410 of "There is no found schema information. Do you want to download the schema information?" and download the schema information preset to the corresponding sensing apparatus according to the user's selection for an acceptance button 420 or a cancellation button 430 located at one side of the corresponding sentences.

For example, when the user presses the acceptance button 420, the schema information is downloaded. When the user presses the cancellation button 430, the corresponding schema information is not downloaded.

As illustrated in FIG. 4B, when the collection apparatus does not have the schema information preset to the corresponding sensing apparatus, the collection apparatus may display sentences 440 of "There is no found schema information. The schema information will be downloaded." and then download the schema information.

At this time, an OK button 450 for confirming the download is located at one side of the corresponding sentences 440.

The display unit 125 may display a screen related to the application and display the lifelog data of the preset schema through the displayed application.

The storage unit 126 may store the lifelog data collected from the sensing apparatus. The storage unit 125 may store the lifelog data of the first schema corresponding to low data collected from the sensing apparatus or store the lifelog data of the second schema converted to the preset schema.

Figure 5:
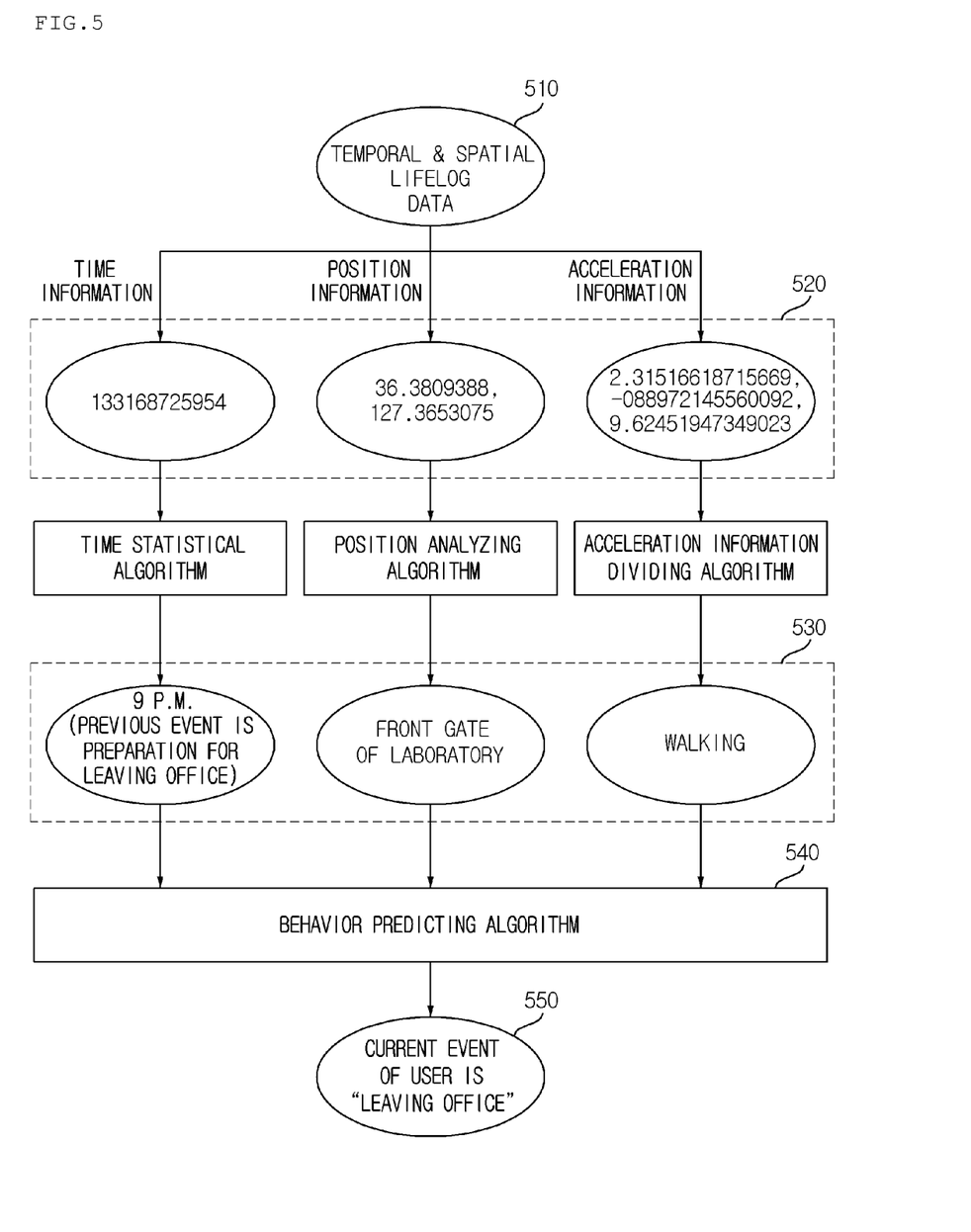
FIG. 5 illustrates an example of applying lifelog data according to an exemplary embodiment of the present invention.

FIG. 5 illustrates an example of applying the lifelog data according to an exemplary embodiment of the present invention.

As illustrated in FIG. 5, a process of predicting a user's behavior by using the lifelog data will be described. First, when the application is activated in the collection apparatus, the application may collect the lifelog data from at least one sensing apparatus (in 510).

The application may divide the collected lifelog data into time information, position information, and acceleration information (in 520).

The application may divide each of the divided information into data required to predict the user's behavior by using an algorithm (in 530).

For example, 1) the time information is divided into 9 a.m., 9 p.m. and the like according to a time, 2) the position information is divided into an office, a road, a dormitory, a restaurant and the like according to a current position, and 3) the acceleration information is divided into walking, sitting, standing, running, and the like.

The application may analyze the user's state at a current time by using a behavior predicting algorithm based on the divided data, such as 9 p.m., a front gate of a laboratory, and walking (in 540).

The application predicts the user's behavior by using the analyzed current state of the user, for example, a normal behavior that the user leaves the office to go to the dormitory on foot at 9 p.m. (in 550).

Accordingly, the application may display a current event of the user as "leaving the office".

Figure 6:
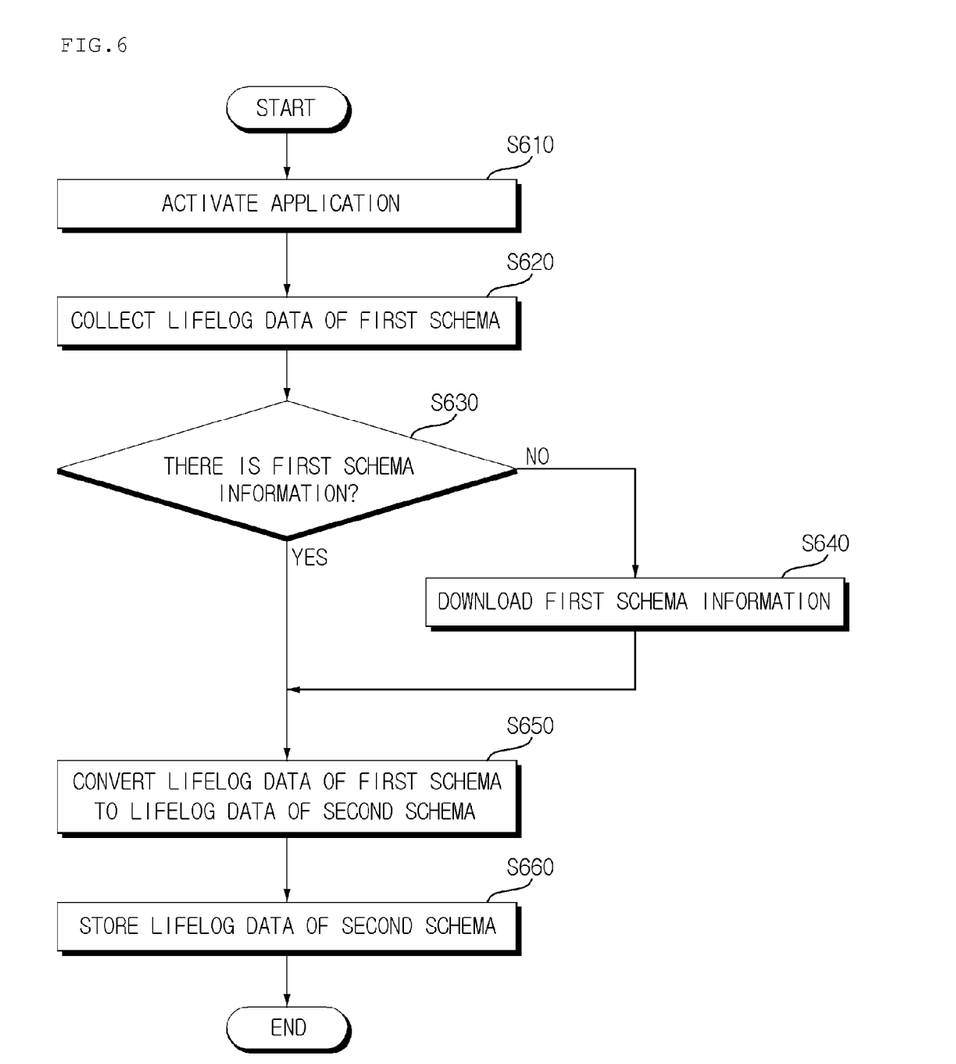
FIG. 6 illustrates a method of collecting lifelog data according to an exemplary embodiment of the present invention.

FIG. 6 illustrates a method of collecting the lifelog data according to an exemplary embodiment of the present invention.

As illustrated in FIG. 6, the collection apparatus according to the present invention may activate an application according to user's selection (in S610) and activate the lifelog data through the activated application (in S620).

Next, the collection apparatus may identify whether to have schema information of the collected lifelog data (in S630).

Next, when the collection apparatus has the schema information, the collection apparatus converts the lifelog data of the first schema to the lifelog data of the preset second schema (S650).

On the other hand, when the collection apparatus does not have the schema information, the collection apparatus accesses the schema server to download first schema information from the accessed schema server (in S640) and converts the lifelog data of the downloaded first schema to the lifelog data of the preset second schema (S650).

Next, the collection apparatus may store the converted lifelog data of the second schema (S660).

Meanwhile, the embodiments according to the present invention may be implemented in the form of program instructions that can be executed by computers, and may be recorded in computer readable media. The computer readable media may include program instructions, a data file, a data structure, or a combination thereof. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An apparatus for collecting lifelog data, comprising:
   an input unit receives information according to a menu or key control from a user;
   a controller activates an application according to the received information, activates the lifelog data through the activated application, determines to have schema information of collected lifelog data, collects measured lifelog data of a first schema from one or more sensing apparatuses through the application activated according to the received information and converts the collected lifelog data of the first schema to lifelog data of a preset second schema;
   a display unit displays an analysis result of a behavior of the user through the application based on the converted lifelog data of the second schema;
   a storage unit stores the lifelog data of the first schema or the lifelog data of the second schema; and
   a communication unit transmits the lifelog data of the first schema or the lifelog data of the second schema to a lifelog server configured to manage the lifelog data for each user,
   wherein the application processes data based on the lifelog data of the second schema,
   wherein the first schema is differently set for each of the sensing apparatuses,
   wherein the lifelog server provides the lifelog data of the second schema requested by a management server to the management server, or the lifelog server converts the lifelog data of the first schema receiving from the communication unit to the lifelog data of the second schema requested by the management server and provides corresponding lifelog data of the second schema to the management server,
   wherein the management server is configured to provide a service to each of the users based on corresponding lifelog data.

2. The apparatus of claim 1, wherein, when the lifelog data is collected, the controller identifies whether to have first schema information of the collected lifelog data, and when the controller has the first schema information as a result of the identification, the controller converts the lifelog data of the first schema to the lifelog data of the second schema by using the first schema information.

3. The apparatus of claim 1, wherein, when the lifelog data is collected, the controller identifies whether to have first schema information of the collected lifelog data, and when the controller does not have the first schema information as a result of the identification, the controller downloads the first schema information from a schema server and converts the lifelog data of the first schema to the lifelog data of the second schema by using the downloaded first schema information.

4. The apparatus of claim 3, wherein the display unit displays a sentence of informing the user that the first schema information is automatically downloaded from the schema server and an OK button for confirming the download at one side of the sentence.

5. The apparatus of claim 1, wherein, when the lifelog data is collected, the controller identifies whether to have first schema information of the collected lifelog data, and when the controller does not have the first schema information as a result of the identification, the controller asks the user about whether to download the first schema information from the schema server and downloads the first schema information according to an input selection of the user in response to an inquiry.

6. The apparatus of claim 5, wherein the display unit displays a sentence of asking the user about whether to download the first schema information from the schema server and displays an acceptance button of accepting the download and a cancellation button of cancelling the download at one side of the sentence.

7. The apparatus of claim 1, wherein the controller collects the measured lifelog data according to schema information preset to each of the one or more sensing apparatuses.

8. A method of collecting lifelog data, comprising:
   activating an application according to a user's selection;
   activating the lifelog data through the activated application;
   determining to have schema information of collected lifelog data;
   collecting measured lifelog data of a first schema from one or more sensing apparatuses through the activated application and converting the collected lifelog data of the first schema to lifelog data of a preset second schema;
   displaying an analysis result of a behavior of a user through the application based on the converted lifelog data of the second schema;
   storing the lifelog data of the first schema or the lifelog data of the second schema; and
   transmitting the lifelog data of the first schema or the lifelog data of the second schema to a lifelog server configured to manage the lifelog data for each user,
   wherein the application processes data based on the lifelog data of the second schema,
   wherein the first schema is differently set for each of the sensing apparatuses,
   wherein the lifelog server provides the lifelog data of the second schema requested by a management server to the management server, or the lifelog server converts the lifelog data of the first schema receiving from the communication unit to the lifelog data of the second schema requested by the management server and provides corresponding lifelog data of the second schema to the management server,
   wherein the management server is configured to provide a service to each of the users based on corresponding lifelog data.

9. The method of claim 8, wherein, in the converting of the collected lifelog data, when the lifelog data is collected, it is identified whether to have first schema information of the collected lifelog data, and when it is identified to have the first schema information as a result of the identification, the lifelog data of the first schema is converted to the lifelog data of the second schema by using the first schema information.

10. The method of claim 8, wherein, in the converting of the collected lifelog data, when the lifelog data is collected, it is identified whether to have first schema information of the collected lifelog data, and when it is identified not to have the first schema information as a result of the identification, the first schema information is downloaded from a schema server and the lifelog data of the first schema is converted to the lifelog data of the second schema by using the downloaded first schema information.

11. The method of claim 10, wherein, in the converting of the collected lifelog data, a sentence of informing the user that first schema information is automatically downloaded from the schema server is displayed and an OK button for confirming the download is displayed at one side of the sentence.

12. The method of claim 8, wherein, in the converting of the collected lifelog data, when the lifelog data is collected, it is identified whether to have first schema information of the collected lifelog data, and when it is identified not to have the first schema information as a result of the identification, the user is asked whether to download the first schema information from the schema server and the first schema information is downloaded according to an input selection of the user in response to an inquiry.

13. The method of claim 12, wherein, in the converting of the collected lifelog data, a sentence of asking the user about whether to download the first schema information from the schema server is displayed and an acceptance button of accepting the download and a cancellation button of cancelling the download are displayed at one side of the sentence.

14. The method of claim 8, wherein, in the converting of the collected lifelog data, the measured lifelog data is collected according to schema information preset to each of the one or more sensing apparatuses.

* * * * *